US008772712B2

(12) United States Patent
Kimura et al.

(10) Patent No.: US 8,772,712 B2
(45) Date of Patent: Jul. 8, 2014

(54) ANALYSIS APPARATUS AND ANALYSIS METHOD

(71) Applicant: Semiconductor Energy Laboratory Co., Ltd., Atsugi (JP)

(72) Inventors: Hajime Kimura, Atsugi (JP); Shunsuke Kiyomura, Atsugi (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

(21) Appl. No.: 13/863,698

(22) Filed: Apr. 16, 2013

(65) Prior Publication Data

US 2013/0277549 A1 Oct. 24, 2013

(30) Foreign Application Priority Data

Apr. 24, 2012 (JP) .................................. 2012-099032

(51) Int. Cl.
*H01J 49/40* (2006.01)
*H01J 49/42* (2006.01)
*H01J 49/26* (2006.01)

(52) U.S. Cl.
USPC ........... 250/309; 250/283; 250/285; 250/306; 250/492.21

(58) Field of Classification Search
USPC ...................... 250/283, 285, 306, 309, 492.21
See application file for complete search history.

(56) References Cited

U.S. PATENT DOCUMENTS

| 4,851,669 | A | * | 7/1989 | Aberth | 250/281 |
| 5,087,815 | A | * | 2/1992 | Schultz et al. | 850/63 |
| 5,527,731 | A | * | 6/1996 | Yamamoto et al. | 250/492.3 |
| 6,989,528 | B2 | * | 1/2006 | Schultz et al. | 250/281 |
| 7,629,576 | B2 | * | 12/2009 | Schultz et al. | 250/287 |
| 7,825,389 | B2 | * | 11/2010 | Hautala et al. | 250/492.3 |
| 8,008,619 | B2 | * | 8/2011 | Jolliffe et al. | 250/285 |
| 8,410,425 | B2 | * | 4/2013 | Kollmer et al. | 250/282 |
| 8,481,931 | B2 | * | 7/2013 | Page | 250/306 |

(Continued)

FOREIGN PATENT DOCUMENTS

| JP | 2008-175654 A | 7/2008 |
| JP | 2008-544231 A | 12/2008 |

(Continued)

OTHER PUBLICATIONS

M. Kudo, K. Aimoto, N. Kato, S. Aoyagi, N. Iida, and A. Yamamoto, "Enhancement of Secondary Ion Intensities from Polymers in the TOF-SIMS Analysis using Gold Cluster Ions," Journal of the Surface Science Society of Japan, 2006, vol. 27, No. 9, pp. 518-522.

*Primary Examiner* — David A Vanore
(74) *Attorney, Agent, or Firm* — Eric J. Robinson; Robinson Intellectual Property Law Office, P.C.

(57) ABSTRACT

A compound contained in a sample is analyzed more accurately. Provided is an analysis method using TOF-SIMS in which first spectral data is obtained by irradiating the sample with a first primary ion, second spectral data is obtained by irradiating the sample with a second primary ion, and a surface of the sample is etched by an ion and then the surface of the sample is irradiated with the first primary ion or the second primary ion. The first primary ion is more likely to break a molecular structure of a molecule contained in the sample than the second primary ion.

15 Claims, 3 Drawing Sheets

(56) References Cited

U.S. PATENT DOCUMENTS

| | | | |
|---|---|---|---|
| 8,525,125 B1* | 9/2013 | Kollmer et al. | 250/423 R |
| 2009/0152457 A1* | 6/2009 | Niehuis et al. | 250/282 |
| 2010/0237234 A1* | 9/2010 | Kollmer et al. | 250/282 |
| 2011/0114926 A1 | 5/2011 | Okabe et al. | |
| 2011/0269619 A1* | 11/2011 | Verbeck et al. | 502/5 |
| 2012/0018630 A1* | 1/2012 | Schultz et al. | 250/282 |
| 2012/0125889 A1* | 5/2012 | Toyoda et al. | 216/57 |
| 2013/0216427 A1* | 8/2013 | Kollmer et al. | 420/577 |

FOREIGN PATENT DOCUMENTS

| | | |
|---|---|---|
| JP | 2010-067960 A | 3/2010 |
| JP | 2011-501367 A | 1/2011 |
| JP | 2011-029043 A | 2/2011 |

* cited by examiner

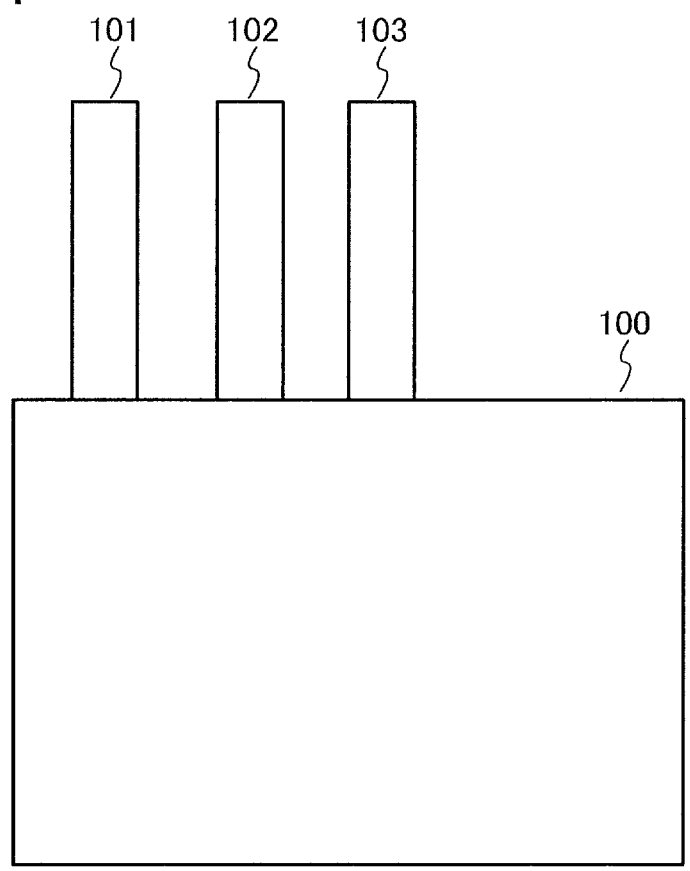

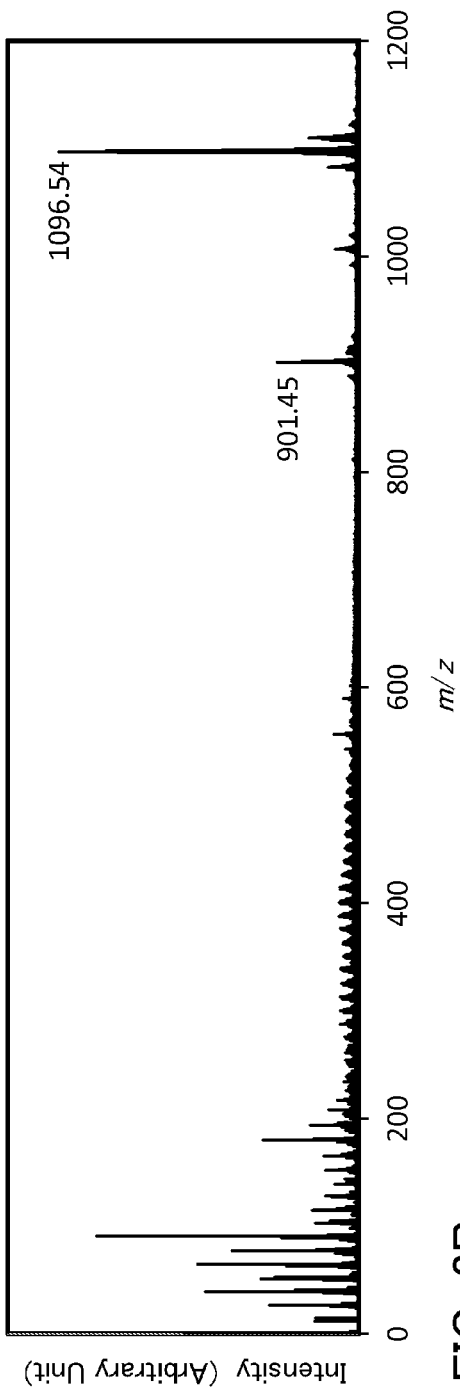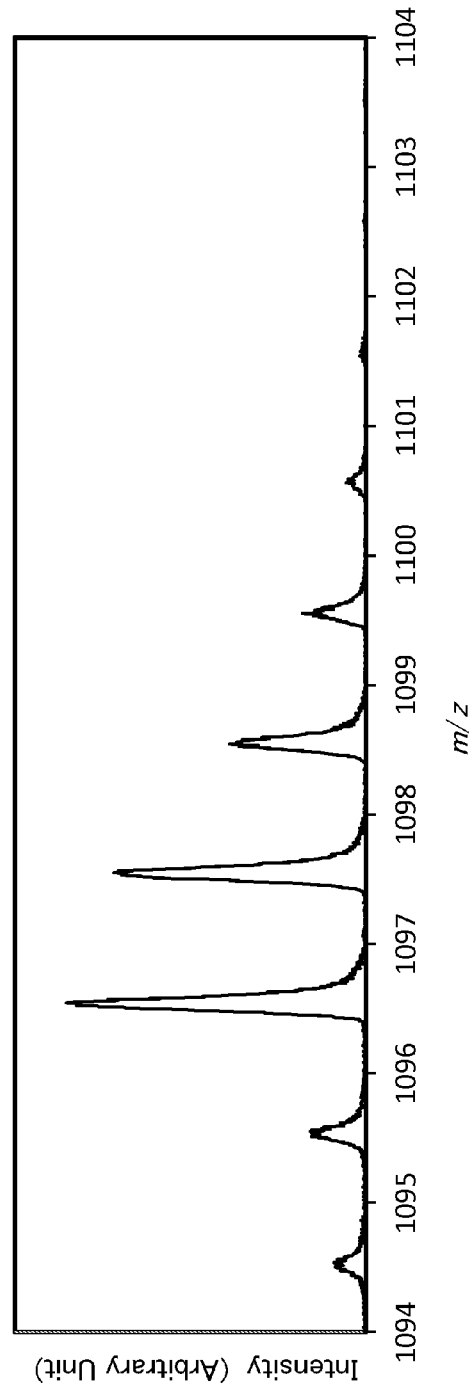

ANALYSIS APPARATUS AND ANALYSIS METHOD

BACKGROUND OF THE INVENTION

1. Field of the Invention

One embodiment of the present invention relates to an analysis method, an analysis apparatus, an analysis technology, a data processing apparatus, or a data processing method. In particular, one embodiment of the present invention relates to an analysis method, an analysis apparatus, an analysis technology, a data processing apparatus, or a data processing method intended for an organic compound. In particular, one embodiment of the present invention relates to an analysis method, an analysis apparatus, an analysis technology, a data processing apparatus, or a data processing method intended for a display device, a light-emitting device, or a lighting device which includes an organic EL element. In particular, one embodiment of the present invention relates to an apparatus and a method using TOF-SIMS. In particular, one embodiment of the present invention relates to an apparatus and a method for an analysis of a sample surface. In particular, one embodiment of the present invention relates to an apparatus and a method for an analysis in which a sample surface is irradiated with ions.

2. Description of the Related Art

In recent years, a light-emitting element including an organic compound such as an organic EL element, and further, a display device or a lighting device including the light-emitting element have been developed. An organic EL element includes an organic material sandwiched between a cathode and an anode. Thus, as a method for analyzing the organic material, a time-of-flight secondary ion mass spectrometry (TOF-SIMS) or the like is used.

TOF-SIMS is time-of-flight secondary ion mass spectrometry, in which a sample surface is irradiated with primary ions, and thereby secondary ions released from the sample are detected. The distance between the sample and a detector is constant. An ion with low mass reaches the detector earlier than an ion with high mass. Thus, by measuring time to reach the detector (flight time of secondary ions), mass of molecules contained in a sample can be measured (e.g., Patent Documents 1 to 5 and Non-Patent Document 1).

REFERENCE

Patent Document

[Patent Document 1] Japanese Published Patent Application No. 2008-175654
[Patent Document 2] Japanese Published Patent Application No. 2010-67960
[Patent Document 3] Japanese Published Patent Application No. 2011-29043
[Patent Document 4] Japanese Translation of PCT International Application No. 2011-501367
[Patent Document 5] Japanese Translation of PCT International Application No. 2008-544231

Non-Patent Document

[Non-Patent Document 1] M. Kudo, K. Aimoto, N. Kato, S. Aoyagi, N. Iida, and A Yamamoto: "Enhancement of Secondary Ion Intensities from Polymers in the TOF-SIMS Analysis using Gold Cluster Ions", Journal of The Surface Science Society of Japan, 2006, Vol. 27, No. 9, pp. 518-522

SUMMARY OF THE INVENTION

An object of one embodiment of the present invention is to analyze a compound contained in a sample more accurately. Another object of one embodiment of the present invention is to analyze a plurality of compounds contained in a sample more accurately. Another object of one embodiment of the present invention is to measure molecular weight of each of a plurality of compounds contained in a sample more accurately. Another object of one embodiment of the present invention is to measure the number of kinds of compounds contained in a sample more accurately. Another object of one embodiment of the present invention is to measure the number (the density) of molecules of each of a plurality of compounds contained in a sample as accurately as possible. Another object of one embodiment of the present invention is to determine the ratio (the mixture ratio) of the number of molecules between a plurality of compounds contained in a sample as accurately as possible.

Note that the descriptions of these objects do not disturb the existence of other objects. Note that in one embodiment of the present invention, there is no need to achieve all the objects. Other objects will be apparent from and can be derived from the description of the specification, the drawings, the claims, and the like.

One embodiment of the present invention is an analysis apparatus including a first ion source and a second ion source. The first ion source has a function of irradiating a sample with a first primary ion. The second ion source has a function of etching the sample in the depth direction and a function of irradiating the sample with a second primary ion.

Another embodiment of the present invention is, in the above structure, an analysis apparatus in which the first primary ion is more likely to break the molecular structures of molecules contained in the sample into a larger numbers of pieces (fragments) than the second primary ion.

Another embodiment of the present invention is, in the above structure, an analysis apparatus which has a function of performing data processing with the use of a first spectral data obtained by using the first primary ions and a second spectral data obtained by using the second primary ions.

Another embodiment of the present invention is, in the above structure, an analysis apparatus in which the data processing includes processing to obtain a product of the first spectral data and the second spectral data.

Another embodiment of the present invention is an analysis method using TOF-SIMS in which a first spectral data and a second spectral data are obtained by irradiating a sample with a first primary ion and a second primary ion, respectively. The first primary ion is more likely to break the molecular structures of molecules contained in the sample than the second primary ion.

Another embodiment of the present invention is an analysis method using TOF-SIMS in which a first spectral data and a second spectral data are obtained by irradiating a sample with a first primary ion and a second primary ion, respectively. The first primary ion is more likely to break the molecular structures of molecules contained in the sample than the second primary ion. A surface of the sample is etched by ions and then is irradiated with the first primary ion or the second primary ion.

Another embodiment of the present invention is an analysis method using TOF-SIMS in which a first spectral data and a second spectral data are obtained by irradiating a sample with a first primary ion and a second primary ion, respectively. The first primary ion is more likely to break the molecular structures of molecules contained in the sample than the second primary ion. A surface of the sample is etched by ions including the same elements as the second primary ion.

Another embodiment of the present invention is, in the above structure, an analysis method in which analysis results are evaluated by comparing the first spectral data obtained by using the first primary ion with the second spectral data obtained by using the second primary ion.

Another embodiment of the present invention is, in the above structure, an analysis method in which data processing is performed using the first spectral data obtained by using the first primary ion and the second spectral data obtained by using the second primary ion.

Another embodiment of the present invention is, in the above structure, an analysis method in which the data processing includes processing to obtain a product of the first spectral data and the second spectral data.

Note that an ion source is, for example, a source (an ion source) for ionizing a sample, a part where an ion is generated, or a part for irradiating with an ion. Accordingly, a first primary ion source includes a first primary ion, for example. Alternatively, a first primary ion source contains an original material for generating a primary ion. Alternatively, a first primary ion source has a function of generating a first primary ion or irradiating with a first primary ion. Note that for simplification, an ion source may be referred to as just an ion, and an ion may be referred to as an ion source.

In one embodiment of the present invention, a compound contained in a sample can be analyzed more accurately. In another embodiment of the present invention, a plurality of compounds contained in a sample can be analyzed more accurately. In another embodiment of the present invention, molecular weight of each of a plurality of compounds contained in a sample can be measured more accurately. In another embodiment of the present invention, the number of kinds of compounds contained in a sample can be measured more accurately. In another embodiment of the present invention, the number (the density) of molecules of each of a plurality of compounds contained in a sample can be measured as accurately as possible. In another embodiment of the present invention, the ratio (the mixture ratio) of the number of molecules between a plurality of compounds contained in a sample can be determined as accurately as possible.

BRIEF DESCRIPTION OF THE DRAWINGS

In the accompanying drawings:
FIG. 1 is a diagram illustrating a TOF-SIMS apparatus;
FIGS. 3A and 3B are results of a TOF-SIMS analysis using $Bi_3^+$ as a primary ion.

DETAILED DESCRIPTION OF THE INVENTION

Figure 2A:
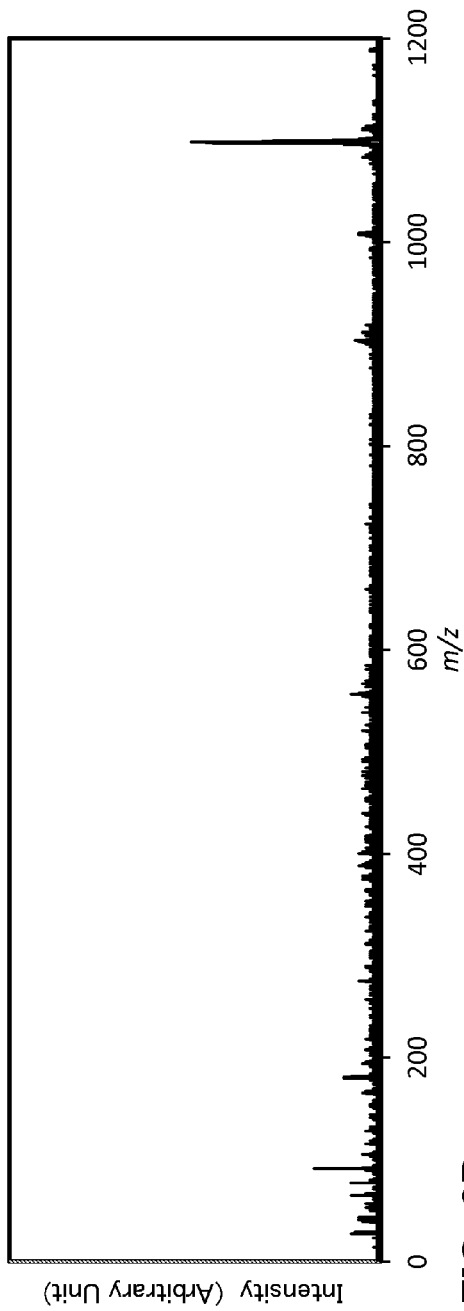
FIGS. 2A and 2B are results of a TOF-SIMS analysis using an argon cluster ion as a primary ion.

Embodiments will be described below. However, the embodiments can be implemented with various modes. It will be readily appreciated by those skilled in the art that modes and details can be changed in various ways without departing from the spirit and scope of the present invention. Therefore, this invention is not interpreted as being limited to the description of the embodiments below. Note that in structures of the invention described below, the same portions or portions having similar functions are denoted by the same reference numerals, and description thereof is not repeated.

Note that what is described (or part thereof) in one embodiment can be applied to, combined with, or exchanged with another content in the same embodiment and/or what is described (or part thereof) in another embodiment or other embodiments.

Note that in each embodiment, a content described in the embodiment is a content described with reference to a variety of diagrams or a content described with a paragraph disclosed in this specification.

In addition, by combining a diagram (or part thereof) described in one embodiment with another part of the diagram, a different diagram (or part thereof) described in the same embodiment, and/or a diagram (or part thereof) described in one or a plurality of different embodiments, much more diagrams can be formed.

The invention excluding content which is not specified in the drawings and texts in this specification can be constituted. Alternatively, when the range of a value (e.g., the maximum and minimum values) is described, part of the range is arbitrarily shortened and part of the range is removed, so that an invention can be specified by a range part of which is removed from the number range. In this manner, it is possible to specify the scope of the present invention so that a conventional technology is excluded, for example.

As another specific example, a description says about a stacked structure that "a film is provided between A and B". In this case, for example, it can be specified that in an invention, the film is not a stacked film of four or more layers. Alternatively, for example, it can be specified that in an invention, a conductive film is not provided between A and the film.

Ordinal numbers such as "first" and "second" are added for avoiding confusion between components and the number of components is not limited to the number of ordinal numbers.

Embodiment 1

In this embodiment, an example in which analyses are performed plural times using a plurality of primary ion sources (primary ions) is described. An example in which an analysis is performed using, as two ion sources (ions), a first primary ion source (primary ion) and a second primary ion source (primary ion) is described. Note that one aspect of one embodiment of the present invention is not limited to this example; it is possible to use one ion source (ion) or three or more ion sources (ions).

First, a TOF-SIMS analysis is performed on a sample using the first primary ion source, whereby first spectral data (a spectrum having peaks each corresponding to the mass number derived from a chemical structure) is obtained. Next, the primary ion source is changed and a TOF-SIMS analysis is performed on the sample using the second primary ion source to obtain second spectral data.

Note that the measurement sequence is not limited to this; an analysis using the first primary ion source can be performed after an analysis using the second primary ion source, the reverse sequence is possible, or the two analyses can be performed at the same time.

Here, the second primary ion source (primary ion) is larger than or heavier than the first primary ion source (primary ion). In the case of a cluster ion, the number of atoms of the second primary ion source is larger than that of the first primary ion source (primary ion). Alternatively, the second primary ion source (primary ion) does not easily break the structures of molecules contained in a sample than the first primary ion source (primary ion) or the like is used. Alternatively, as the second primary ion source (primary ion), one whose energy per ion is smaller than that of the first primary ion source (primary ion) or the like is used. Alternatively, the second primary ion source (primary ion) having a wider distribution (variation) of cluster sizes (the number of atoms contained in a cluster ion) than that of the first primary ion source (primary ion) or the like is used.

Then, the first spectral data is compared with the second spectral data. Alternatively, analysis results are evaluated by comparing the first spectral data with the second spectral data. Alternatively, data processing is performed using the first spectral data and the second spectral data.

First considered is the second spectral data. In the case of using the second primary ion source (primary ion), the number of peaks detected in the second spectral data is smaller than the number of peaks detected in the first spectral data, because the second primary ion source (primary ion) does not easily break the molecular structures of a sample. In some cases, in the second spectral data, the intensity of a peak on the high mass number side is increased. However, in the case where the primary ion is a cluster ion, for example, there may be a case where the distribution of cluster sizes is wide (i.e., the variation of the number of atoms contained in a cluster is wide) and thus the mass of molecules in the second spectral data is detected at low resolution. There may be another case where the ionization rate is low and thus the intensities of peaks in the second spectral data are low and the S/N ratio is insufficient. There may be another case where, in the second spectral data, the intensities of peaks on the low mass number side are low and thus it is difficult to determine whether there is a peak or not.

On the other hand, in the first spectral data, the molecular structures in a sample are more likely to be broken; thus, it is difficult in some cases to determine whether a peak is derived from a component inherently contained in a sample, or from a part of fragments of a broken molecular structure, a broken crystal structure, or a dissociated crystal structure. In some cases, in the first spectral data, the intensity of a peak on the low mass number side is decreased. However, in the case where the primary ion is a cluster ion, there may be a case where the distribution of cluster sizes is narrow (i.e., the variation of the number of atoms contained in a cluster is small) and thus the mass of molecules in the first spectral data is detected at high resolution. There may be another case where the ionization rate is high and thus the intensities of peaks in the first spectral data are high and the S/N ratio is sufficient. There is a case in which, in the first spectral data, the intensities of peaks on the low mass number side are increased and thus it is easy to judge that the peak is significant.

In other words, in some cases, the first spectral data and the second spectral data have a mutually complementary relation; a weakness of one of the first spectral data and the second spectral data can be complemented by a strength of the other thereof. For example, in the case where a peak found in the first spectral data is not found in the second spectral data, it can be judged that the peak is derived from fragmentation of a broken molecular structure. Thus, in the case where a molecule before being broken by a primary ion needs to be identified, a peak in the first spectral data which appears not to be found in the second spectral data can be ignored as not existing. Accordingly, data of only molecules (a parent peak data) contained in a sample can be extracted.

Conversely, in the case where a peak found in the second spectral data is not found in the first spectral data, it can be judged that the peak is derived from low mass resolution or insufficient S/N ratio. Thus, in the case where the mass number of a molecule before being broken by a primary ion needs to be identified, the mass number can be estimated from a peak found in the second spectral data which is also found in the first spectral data.

In other words, spectral data in which molecular structures are not broken or the amount or proportion of broken molecular structures is small can be obtained from the second spectral data. Thus, even when a sample contains various molecules, data on how many kinds of molecules are contained can be obtained. Then, molecular mass (m/z) can be obtained from the first spectral data accurately to some extent.

In this manner, by using the first spectral data and the second spectral data, the mass number (m/z) of molecule contained in a sample can be accurately obtained and data of a fragmented molecule which is broken by a primary ion can be removed so that data other than original data of a sample is not included.

Accordingly, even when various molecules are contained in a sample, the number (density) of each molecule and the ratio (mixture ratio) of each molecule can be obtained accurately to some extent.

When such data processing is performed by calculation, various methods can be used. For example, new processed data can be obtained by multiplying the first spectral data by the second spectral data. In the case where a value in the second spectral data is not found (a value is extremely small), the value is zero (extremely small) in processed data; thus, processed data from which an unnecessary peak is removed can be obtained from the first spectral data.

Note that in this case, normalization processing may be performed on one or both of the first spectral data and the second spectral data. That is, the whole data may be normalized so that the maximum value of the spectral data is a certain value (e.g., 1, 100, or the like). For example, data normalized to 1 can be obtained by dividing each value of data by the maximum value of the data. In the case where there is a large difference between the peak intensity of the first spectral data and the peak intensity of the second spectral data, each data is normalized and then multiplied, thereby obtaining new processed data. Thus, an analysis of the processed data becomes easier.

For example, only the second spectral data is normalized to 1 and a product of the normalized data and the first spectral data is obtained; thus, a peak derived from a fragment can be easily removed from the first spectral data.

Alternatively, new processed data can be obtained by performing binarization process on the second spectral data and then performing various processes. There may be a case in which the mass resolution for the second spectral data is low; therefore, the peak maximum does not necessarily correspond to the molecular mass. Thus, binarization process in which values are divided into two groups of values depending on whether it is greater than or equal to, or smaller than a given threshold value is performed. As a result, an analysis of the processed data becomes easier.

For example, the second spectral data is binarized and then a product is obtained by multiplying the binarized data by the first spectral data, whereby a peak derived from a fragment can be easily removed from the first spectral data.

Note that in the case where binarization process is performed, the first spectral data may also be subjected to binarization process. In this case, a logical product (AND) of the first spectral data and the second spectral data can be obtained. That is, data detected in both of the first spectral data and the second spectral data can be assumed as data of molecules contained in a sample.

Note that although multiplication is used in data processing for obtaining processed data, one embodiment of the present invention is not limited to this. For example, new processed data can be obtained by addition or logical addition (OR) of the first spectral data and the second spectral data. When values are obtained in both of the first and the second spectral data, the values are to be large, in which case processed data from which molecules are assumed as those before the molecule structures are broken can be obtained.

Even when various molecules are contained in a sample, by performing the above data processing, the number of kinds of molecules contained in the sample, molecular weight, the number (density) of molecules, or the ratio (mixture ratio) of the numbers of molecules can be determined on each of the various molecules.

Note that the above-described data processing can be performed using dedicated hardware or software. The software can be stored in a recording medium, such as a CD, a DVD, a flash memory, a hard disk, a semiconductor memory, a magnetic memory, a magneto-optical disk, and an organic memory. Distribution (uploading) or downloading of the software is possible via the network.

Note that as data processing, process of obtaining peak intensities from spectral data can be performed. Further, as the following process, a principal component analysis where the peak intensity is variable can be performed. Furthermore, as the following process, it is possible to obtain a principle component score of the principle component obtained by the principal component analysis and plot the scores on a two-dimensional plane.

Note that when TOF-SIMS analyses are performed using the first primary ion source (primary ion) and the second primary ion source (primary ion), it is desirable to perform the analyses on the same sample. Thus, analyses can be performed more accurately. In other words, the case in which TOF-SIMS analyses using the first primary ion source (primary ion) to an M-th primary ion source (primary ion) are performed plural times (e.g., M times; M is a natural number, here) on the same sample is described in this embodiment; however, one embodiment of the present invention is not limited to this, and TOF-SIMS analyses may be performed on different samples. For example, of the M times of TOF-SIMS analyses, it is possible to perform TOF-SIMS analyses on a sample A at most M−1 times or less, and on a sample B which is different from the sample A at least once. In this case, the sample A and the sample B preferably contain the same material as much as possible. For example, it is preferable that the sample A and the sample B be originally one sample and be divided into two samples by breaking or cutting the original sample. The sample A and the sample B are preferably manufactured at the same time, manufactured under almost the same conditions, have the same product number, the same serial number, or the same model number, or manufactured by the same company or the same organization.

Note that when the same sample is used in analyses using a first primary ion source (primary ion) and a second primary ion source (primary ion), it is desirable that the analyses be performed on different regions of the same sample. Thus, an influence caused when the sample is changed by an analysis can be reduced. Note that one embodiment of the present invention is not limited to this. Analyses using the first primary ion source (primary ion) and the second primary ion source (primary ion) can be performed on the same region of the same sample. In this case, it is preferable that an analysis using the first primary ion source (primary ion) be performed after an analysis using the second primary ion source (primary ion). Since the second primary ion source (primary ion) does not easily break the molecular structures and has a small influence on the sample, an influence caused when a sample is changed by an analysis can be reduced.

Note that one embodiment of the present invention is not limited to the above-described embodiment in which analyses are performed using the first primary ion source (primary ion) and the second primary ion source (primary ion). For example, TOF-SIMS analyses can be performed three times or more using three or more primary ion sources (primary ions). Alternatively, TOF-SIMS analyses can be performed plural times using one primary ion source (primary ion) under different conditions (intensity, current, irradiation time, and the like) of the primary ion source (primary ion).

For example, in the case of using M primary ion source (primary ion), an (N+1)-th primary ion source (primary ion) is larger than or heavier than an N-th primary ion source (primary ion). In the case of a cluster ion, the number of atoms of the (N+1)-th primary ion source is larger than that of the N-th primary ion source (primary ion). Alternatively, the (N+1)-th primary ion source (primary ion) does not easily break the structures of molecules contained in a sample than the N-th primary ion source (primary ion) or the like is used. Alternatively, as the second primary ion source (primary ion), one whose energy per ion is smaller than that of the first primary ion source (primary ion) or the like is used. Alternatively, the (N+1)-th primary ion source (primary ion) having a wider distribution (variation) of cluster sizes (the number of atoms contained in a cluster ion) than that of the N-th primary ion source (primary ion) or the like is used. Here, N is a natural number of smaller than or equal to (M−1).

When a plurality of primary ion sources (primary ions) is used, spectral data can be obtained utilizing advantage of each primary ion source (primary ion). For example, in the case where three primary ion sources (primary ions) are used, a third primary ion source (primary ion) having the advantage of does not easily breaking the molecular structure and the disadvantages of low mass resolution, low ionization rate, and the like is used (note that disadvantages are desirably minimized). As the second primary ion source (primary ion), one which has the advantages of breaking the molecular structures only a very little and high mass resolution and the disadvantage that the ionization rate is not so high is used (note that disadvantages are desirably minimized). As the first primary ion source (primary ion), one which has the advantages of high mass resolution and high ionization rate and the disadvantage of breaking the molecular structures is used (note that disadvantages are desirably minimized). In such a case, three kinds of spectral data can be obtained by using three primary ion sources (primary ions). Further, various types of data processing (multiplication, addition, normalization, binarization, and the like) are performed on the three types of spectral data, so that more accurate data can be obtained.

As data processing, for example, binarization can be performed on an M-th spectral data (e.g., a third spectral data) and an (M−1)-th spectral data (e.g., the second spectral data) and multiplication can be performed on M (e.g., three) spectral data to obtain the product. As a result, a peak derived from a fragmented broken molecular structure can be appropriately removed from the first spectral data.

In this manner, a plurality of spectral data is obtained using a plurality of primary ion sources (primary ions) and data processing is performed, whereby a sample can be analyzed more accurately.

Note that an organic material (in particular, an organic material with large molecular weight) is preferable as a sample for an analysis. As another example, a biologic substance such as a protein, an inorganic material, an insulator, a conductor, a semiconductor, or the like can be analyzed. Alternatively, a mixture thereof (e.g., an organic material partly containing a metal) is preferably used. Further, as specific examples, an aromatic organic compound, a heterocyclic organic compound, an aliphatic organic compound, an organohalogen compound, an organosilicon compound, an ester compound, an ether compound, a nitrogen-containing compound, an amino acid, an olefin-based high polymer, an aromatic high polymer, an acrylic high polymer, an ester-based high polymer, a cellulose-based high polymer, a fluorine-based high polymer, an urethane-based high polymer, a long chain alkyl acid, a material containing a plurality of these, or the like is preferable. For example, a film included in an organic EL element, such as an electron injection layer, an electron transport layer, a light-emitting layer, a charge generation layer (which is used for a tandem structure), a hole transport layer, a hole injection layer, an anode electrode, a cathode electrode, an organic layer over a cathode electrode, or the like is preferably used for an analysis.

Examples of an EL element are an element including an anode, a cathode, and an EL layer interposed between the anode and the cathode, and the like. Examples of an EL layer are a layer utilizing light emission (fluorescence) from a singlet exciton, a layer utilizing light emission (phosphorescence) from a triplet exciton, a layer utilizing light emission (fluorescence) from a singlet exciton and light emission (phosphorescence) from a triplet exciton, a layer formed using an organic material, a layer formed using an inorganic material, a layer formed using an organic material and an inorganic material, a layer containing a high-molecular material, a layer containing a low-molecular material, a layer containing a high-molecular material and a low-molecular material, and the like.

As examples of a semiconductor, a compound semiconductor (e.g., SiGe, GaAs, SiC, or the like), an oxide semiconductor (e.g., ZnO, InGaZnO, indium zinc oxide, ITO (indium tin oxide), SnO, TiO, AlZnSnO (AZTO), In—Sn—Zn-based oxide (In—Sn—Zn—O), or the like), and the like are given. In addition, the semiconductors can be in various crystal states, such as an amorphous state, a polycrystalline state, a single crystal state, and the like.

Note that although an analysis by TOT-SIMS is described in this embodiment, one aspect of the embodiment of the present invention is not limited to this. The embodiment of the present invention can be employed for another analysis using ion sources, such as dynamic SIMS, mass spectrometry, a surface analysis, and a depth direction analysis.

This embodiment shows an example of a basic principle. Thus, part or the whole of this embodiment can be freely combined with, applied to, or replaced with part or the whole of another embodiment.

Embodiment 2

In this embodiment, an example of a primary ion source (primary ion) is described. Note that the description is just an example and another primary ion source (primary ion) can be used.

As an example, the case in which two primary ion sources (primary ions) (a first primary ion source (primary ion) and a second primary ion source (primary ion)) are used is described.

As the first primary ion source (primary ion), for example, a monatomic ion such as $Ga^+$, $Cs^+$, $Au^+$, $Bi^+$, $In^+$, or the like; a polyatomic ion such as $SF_5^+$, $SF_n^+$, $Au_3^+$, $Au_n^+$, $Bi_2^+$, $Bi_3^+$, $Bi_n^+$, $O_2^+$, $O_n^+$, $ReO_4^-$, $C_{60}^+$, $C_n^+$, $Ir_4(CO)_{12}$, $Ir_4(CO)_7^+$, $Os_3(CO)_{12}$, $[Pt_9(CO)_{22}]^{2-}$, $[Pt_{19}(CO)_{22}]^{4-}$, $[Ni_{38}Pt_6(CO)_{48}H_{6-n}]^{n-}$, $[100H+(H_2O)_{90000}]^{100+}$, or the like; a cluster ion; a metal cluster complex, a charged droplet, or a mixture thereof. Note that n is a natural number, here. Note that an ion is not only a monovalent ion, but also a divalent ion, a trivalent ion, and the like. In this case, the effective acceleration energy is double or triple the normal; thus, an analysis with a higher spatial resolution (e.g., 100 nm or less) is possible.

As the second primary ion (primary ion), for example, a cluster ion containing a plurality of atoms (e.g., a Group 18 element (a rare gas) such as Ar, Kr, Xe, Rn, and Uuo; Au; C) can be used. Alternatively, as the second primary ion source (primary ion), for example, a metal cluster complex, such as $Ir_4(CO)_{12}$, $Ir_4(CO)_7^+$, $Os_3(CO)_{12}$, $[Pt_9(CO)_{22}]^{2-}$, $[Pt_{19}(CO)_{22}]^{4-}$, or $[Ni_{38}Pt_6(CO)_{48}H_{6-n}]^{n-}$, can be used. Alternatively, as the second primary ion source (primary ion), for example, a charged droplet such as $[100H+(H_2O)_{90000}]^{100+}$ can be used.

Here, for example, in the case where cluster ions are used as both of the first primary ion source (primary ion) and the second primary ion source (primary ion), the number of atoms of the cluster ion of the second primary ion source (primary ion) is preferably larger than the number of atoms of the cluster ion of the first primary ion source (primary ion). It is also preferable that atomic weight of the cluster ion of the second primary ion source (primary ion) be larger than atomic weight of the cluster ion of the first primary ion source (primary ion).

Note that in the case where a cluster ion containing a plurality of atoms is used as the second primary ion source (primary ion), the number of atoms may differ depending on the cluster ions. That is, the sizes of the cluster ions may have a wide distribution (variation), e.g., ranging from several hundred to several thousand atoms per cluster.

Thus, it is preferable that the first primary ion source (primary ion) have less variation of the number of atoms than the second primary ion source (primary ion), for example.

Note that for example, a $C_{60}^+$ cluster ion can be used as the first primary ion source (primary ion) when the number of atoms of the cluster ion of the second primary ion source (primary ion) is large. On the other hand, when the second primary ion source (primary ion) is a monatomic ion or is a cluster ion with a small number of atoms, a $C_{60}^+$ cluster ion can be used as the second primary ion source (primary ion).

Note that an ion other than a $C_{60}^+$ cluster ion can be used as the second primary ion source (primary ion) or the first primary ion source (primary ion). For example, a metal cluster complex, such as $Ir_4(CO)_{12}$, $Ir_4(CO)_7^+$, $Os_3(CO)_{12}$, $[Pt_9(CO)_{22}]^{2-}$, $[Pt_{19}(CO)_{22}]^{4-}$, or $[Ni_{38}Pt_6(CO)_{48}H_{6-n}]^{n-}$; a charged droplet such as $[100H+(H_2O)_{90000}]^{100+}$; or the like can be used as the second primary ion source (primary ion) or the first primary ion source (primary ion).

Alternatively, a primary ion source (primary ion) other than the above can be used.

The case of using three primary ion sources (the first primary ion source, the second primary ion source, and the third primary ion source) is described, which is similar to the case of using two primary ion sources. As the first primary ion source (primary ion), for example, one or more of $Ga^+$, $Cs^+$, $Au^+$, $Bi^+$, $In^+$, $SF_5^+$, $SF_n^+$, $Au_3^+$, $Au_n^+$, $Bi_3^+$, $Bi_n^+$, $O_2^+$, $O_n^+$, $ReO_4^-$, or the like is used. As the second primary ion source (primary ion), for example, one or more of a cluster ion of $SF_5^+$, $SF_n^+$, $Au_3^+$, $Au_n^+$, $Bi_3^+$, $Bi_n^+$, $O_2^+$, $O_n^+$, $ReO_4$, $C_{60}^+$, $C_n^+$, or the like is used. As the third primary ion source (primary ion), a cluster ion of $C_{60}^+$, $C_n^+$, Ar (the number of Ar is 100 or more, preferably from several hundreds to several thousands, further preferably from 1400 to 1600), Au (the number of Au is 100 or more, preferably from several hundreds to several thousands, further preferably from 1400 to 1600), or a Group 18 element (a rare gas) such as Kr, Xe, Rn, and Uuo is used.

Thus, it is preferable that the first primary ion source (primary ion) have less variation of the number of atoms than the second primary ion source (primary ion) or the third primary ion source (primary ion), for example. It is preferable that the second primary ion source (primary ion) have less variation of the number of atoms than the third primary ion source (primary ion).

Thus, for example, a monatomic cluster ion or a cluster ion containing 10 or less atoms can be used as the first primary ion source (primary ion). A cluster ion containing 10 to 100 atoms can be used as the second primary ion source (primary ion). A cluster ion containing 100 or more atoms can be used as the third primary ion source (primary ion). In this case, the cluster size distribution (variation) of the second primary ion source (primary ion) is preferably smaller than the cluster size distribution (variation) of the third primary ion source (primary ion).

In this manner, as the second primary ion source, an ion source which does not easily break the molecular structures of a sample compared with the first primary ion source (primary ion) and which is more likely to break the molecular structures of a sample than the third primary ion source, but has high mass resolution because the cluster size distribution (variation) is small, is used. Thus, an analysis can be performed more accurately.

Note that it is preferable that the cluster size distribution (variation) in the third primary ion source (primary ion) or the second primary ion source (primary ion) be minimized. For example, pulse voltage is applied to a deflection electrode with an appropriate delay time; thus, a cluster ion with a given size can be selected from a cluster ion beam having a wide distribution. For example, the half width can be reduced to about one tenth. For example, delay time (flying time) is set so that two deflection electrodes are opened, whereby the kinetic energy can be controlled in a certain range.

Note that in the case of using three or more primary ion sources (primary ions), the N-th primary ion source (primary ion) appropriately selected from a cluster ion of $Ga^+$, $Cs^+$, $Au^+$, $Bi^+$, $In^+$, $SF_5^+$, $SF_n^+$, $Au_3^+$, $Au_n^+$, $Bi_3^+$, $Bi_n^+$, $O_2^+$, $O_n^+$, $ReO_4^-$, $C_{60}$, $C_n^+$, Ar (the number of Ar is 100 or more, preferably from several hundreds to several thousands, further preferably from 1400 to 1600), Au (the number of Au is 100 or more, preferably from several hundreds to several thousands, further preferably from 1400 to 1600), a Group 18 element (a rare gas) such as Kr, Xe, Rn, and Uuo, or the like can be used. Alternatively, a primary ion source (primary ion) other than the above can be used.

In the same way, irradiation of the primary ions (primary ion source) to a sample is performed at a pulse width of about 10 ns. In order to increase the mass resolution, the primary ions (primary ion sources) may be bunched. It is particularly preferable to bunch the third primary ions (primary ion source) or the second primary ions (primary ion source). In the bunching, at the instant when pulsed ions pass between two plates, voltage is applied to the plate in order to accelerate the pulsed ions, whereby the pulse width can be compressed to about one tenth.

Next, an example of the conditions of the primary ion source (primary ion) is described. The acceleration energy is more than or equal to 1 keV and less than or equal to 80 keV (e.g., about 15 keV). The primary ion current is more than or equal to 100 pA and less than or equal to 1000 pA (in terms of DC), and is about 600 pA (converted to DC) or $10^9$ $A/cm^2$, for example. The irradiation area is preferably more than or equal to 1 µm square and less than or equal to 1000 µm square. The dose of the primary ion is preferably more than or equal to $10^8$ ions/$cm^2$ and less than or equal to $10^{15}$ ions/$cm^2$, further preferably more than or equal to $10^{10}$ ions/$cm^2$ and less than or equal to $10^{13}$ ions/$cm^2$.

This embodiment is obtained by performing change, addition, modification, removal, application, superordinate conceptualization, or subordinate conceptualization on part or the whole of another embodiment. Thus, part of or the whole of this embodiment can be freely combined with, applied to, or replaced with part of or the whole of another embodiment.

Embodiment 3

In this embodiment, an example in which a depth direction analysis (depth profiling) is performed is described.

A depth direction analysis (depth profiling) is preferable when, in the depth direction, different materials are used, the amounts of materials differ, or films are stacked. In such a case, for example, a sample is processed using oblique cutting technique and then subjected to a TOF-SIMS analysis. For example, a sample is precisely cut linearly at a very shallow angle using a surface and interfacial cutting analysis system (SAICAS), a cutting edge of diamond, or the like, and then a linear analysis by TOF-SIMS is performed on the cut cross-sectional surface (inclined surface), whereby the distribution in the depth direction can be checked.

For example, by cutting in an oblique direction, a cut surface in which a pseudo distance in the depth direction is enlarged several tens of times or more, preferably several hundred times or more (e.g., 500 times or more) is formed. Then, a TOF-SIMS analysis is performed on the obtained cut surface with shifting measurement regions. Accordingly, an analysis in the depth direction (depth profiling) can be performed.

Note that in the case where a plurality of primary ion sources (primary ions) (e.g., a first primary ion source (primary ion) and a second primary ion source (primary ion)) is used for a cut cross-sectional surface (inclined surface), analyses are desirably performed on different regions at the same depth of the cut cross-sectional surface (inclined surface). Thus, an influence caused when a sample is changed by an analysis can be reduced. Note that even in the case where analyses are performed on different regions, the regions are preferably as close to each other as possible. Thus, an influence of variation of samples or the cut cross-sectional surfaces (inclined surfaces) can be reduced.

Note that one embodiment of the present invention is not limited to this. Analyses using the first primary ion source (primary ion) and the second primary ion source (primary ion) can be performed on partly or entirely the same region. In this case, it is preferable that an analysis using the first (the N-th) primary ion source (primary ion) be performed after an analysis using the second (the (N+1)-th) primary ion source (primary ion). Since the second (the (N+1)-th) primary ion source (primary ion) has a small influence on the molecular structure of the sample, an influence caused when a sample is changed by an analysis can be reduced.

Note that, another method other than oblique cutting technique can be used for an analysis in the depth direction (depth profiling). For example, a TOF-SIMS analysis is performed first. Then, a sample surface is etched by sputtering ions. After the etching, the sample surface is irradiated with primary ions (primary ion sources) and analyzed by TOF-SIMS. Next, the sample surface is etched by sputtering ions again and then is irradiated with primary ions (primary ion sources) and analyzed by TOF-SIMS. In this manner, an analysis in the depth direction (depth profiling) can be performed by repeating etching and a TOF-SIMS analysis.

Note that the area of the region etched in the depth direction is preferably larger than that of the region irradiated with the primary ions (primary ion sources), preferably 1.5 times or more, further preferably 3 times or more. Thus, molecules are prevented from being mixed from the side surface of the etched region and an analysis can be performed more accurately.

Note that in the case where a plurality of primary ion sources (primary ions) (e.g., a first primary ion source (primary ion) and a second primary ion source (primary ion)) is used, analyses are desirably performed on different regions. Thus, an influence caused when a sample is changed by an analysis can be reduced. Note that even in the case where analyses are performed on different regions, the regions are preferably as close to each other as possible. Thus, an influence of variation of samples or surfaces can be reduced.

Note that in the case where an analysis is performed using a plurality of primary ion sources (primary ions), a sum of areas of measurement regions is preferably smaller than an area of the region etched in the depth direction. An area of the region etched in the depth direction is preferably 1.5 times or more times, further preferably 3 times or more times as large as the sum of areas of the measurement regions.

As a specific example, an area analyzed by TOF-SIMS (an area irradiated with primary ions (primary ion sources)) is 150 μm$^2$ per analysis. In the case where analyses by TOF-SIMS are performed M times using M primary ions (primary ion sources), an area of etched region is 150×(M+1) μm$^2$ or more, or 150×M×2 μm$^2$ or more.

Note that one aspect of one embodiment of the present invention is not limited to these. For example, analyses using the first (the N-th) primary ion source (primary ion) and the second (the (N+1)-th) primary ion source (primary ion) can be performed on partly or entirely the same region. In this case, it is preferable that an analysis using the first (the N-th) primary ion source (primary ion) be performed after an analysis using the second (the (N+1)-th) primary ion source (primary ion). Since the second (the (N+1)-th) primary ion source (primary ion) has a small influence on the molecular structure of the sample, an influence caused when a sample is changed by an analysis can be reduced.

Next, an example of an ion (ion source) for etching in the depth direction is described. As the ion (ion source), a cluster ion of $C_{60}^+$, Ar (the number of Ar is 100 or more, preferably from several hundreds to several thousands, further preferably from 1400 to 1600), or the like is desirably used. Alternatively, an ion source (ion) similar to the M-th primary ion source (primary ion) is desirably used. Thus, a surface of a sample can be removed without breaking the molecular structures of the sample as much as possible.

Note that in the case of using M primary ions (primary ion sources), an M-th primary ion (primary ion source) is preferably similar to the ion (ion source) for etching in the depth direction, and the ion used as the M-th primary ion is larger, heavier, has a larger number of atoms contained in a cluster ion, does not easily break the structure of a molecule contained in a sample, or has low energy per ion or a wide distribution of cluster sizes. As another example, as compared with the ion (ion source) used for etching in the depth direction, the M-th primary ion (primary ion source) may be a little larger, a little heavier, have a little larger number of atoms contained in a cluster ion, less likely to break the structure of a molecule contained in a sample, or have lower energy per ion or a little wider distribution of cluster sizes.

Note that since the ion (ion source) for etching in the depth direction needs to remove a surface, the ion may be different from the M-th primary ion (primary ion source) in that respect.

For example, the energy of the ion (ion source) for etching in the depth direction may be a little higher than that of the M-th primary ion (primary ion source). The ion irradiation time of the ion (ion source) for etching in the depth direction may be longer than that of the M-th primary ion (primary ion source). The irradiation time and the energy of the ion (ion source) for etching in the depth direction may be longer and larger than those of the M-th primary ion (primary ion source). Accordingly, etching in the depth direction can be achieved.

Note that the energy of the ion (ion source) for etching in the depth direction can be increased by increasing the current density, for example.

Note that in the case where the same ion (or an ion containing the same elements) is used as the M-th primary ion (primary ion source) and the ion (ion source) for etching in the depth direction, it is preferable that etching in the depth direction and a TOF-SIMS analysis using the M-th primary ion (primary ion source) be performed successively. Accordingly, the ion sources (ions) can be changed easily and thus measurement can be quickly conducted.

Thus, the following example is possible: a sample surface is etched using Ar cluster ions, a TOF-SIMS analysis is performed using Ar cluster ions as the second primary ion source (primary ion), and a TOF-SIMS analysis is performed using Bi cluster ions as the first primary ion source (primary ion). When the sample surface is etched, it is preferable that the energy of the Ar cluster ions be large and/or the ion irradiation time be long.

This embodiment is obtained by performing change, addition, modification, removal, application, superordinate conceptualization, or subordinate conceptualization on part or the whole of another embodiment. Thus, part of or the whole of this embodiment can be freely combined with, applied to, or replaced with part of or the whole of another embodiment.

Embodiment 4

In this embodiment, an example of an analysis apparatus is shown.

As a TOF mass spectrometer, for example, there are plural kinds of apparatuses with different flight paths, such as a reflectron TOF-SIMS apparatus, a TRIFT TOF-SIMS apparatus, and a spiral orbit TOF-SIMS apparatus. Various apparatuses can be used for an analysis.

Note that the software for data processing described in Embodiment 1 is preferably installed in a TOF-SIMS analysis apparatus or a computer connected to a TOF-SIMS analysis apparatus. For example, the software is preferably installed in a TOF-SIMS apparatus or a semiconductor memory (or a flash memory), a magnetic memory (or hard disk), or the like included in a computer connected to a TOF-SIMS apparatus. Note that one embodiment of the present invention is not limited to this. It is possible to install the software for data processing described in Embodiment 1 in another computer and not to install in a TOF-SIMS analysis apparatus. For example, an analysis agency has a TOF-SIMS analysis apparatus and the software can be installed in a computer of a customer who asks the analysis agency to perform an analysis.

Next, a primary ion source (primary ion) and an ion (ion source) for etching in the depth direction which are included in a TOF-SIMS apparatus are described.

A TOF-SIMS apparatus can include a plurality of ion sources (ions). For example, dual beam structure including two ion sources (ions) is possible, in which case a first one can be used as the ion (ion source) for etching in the depth direction and the second primary ion (ion source) and a second one can be used as the first primary ion (ion source). When the first ion (ion source) is used as the ion (ion source) for etching in the depth direction, the energy is increased (and/or the irradiation time is increased). When the first ion (ion source) is used as the second primary ion (ion source), the energy is lowered (and/or the irradiation time is shortened).

Thus, for example, an Ar cluster ion and a Bi ion are used as the first ion source (ion) and the second ion source (ion), respectively. In this case, the outermost surface is analyzed by TOF-SIMS using Ar cluster ions (the energy is small) and then using Bi ions. Next, the sample surface is etched using Ar cluster ions (the energy is large and/or the irradiation time is long). Subsequently, TOF-SIMS analyses are performed using Ar cluster ions (the energy is small and/or the irradiation time is short) and then using Bi ions. Further, the sample surface is etched using Ar cluster ions (the energy is large and/or the irradiation time is long). Subsequently, TOF-SIMS analyses are performed using Ar cluster ions (the energy is small and/or the irradiation time is short) and then using Bi ions. In the similar manner, an analysis in the depth direction is continued. By the process, analyses can be performed quickly and accurately. Note that one embodiment of the present invention is not limited to these examples.

Note that a TOF-SIMS apparatus can include an ion source (ion) for etching in the depth direction and the primary ion source (primary ion), separately. For example, triple beam structure in which three ion sources (ions) of the ion source (ion) for etching in the depth direction, the first primary ion source (primary ion), and the second primary ion source (primary ion) are included is possible. Note that in the triple beam structure, it is possible to use one ion source (ion) both as the ion source for etching in the depth direction and the third ion source (primary ion). Note that more than three ion sources (ions) can be included in a TOF-SIMS apparatus.

Here, an example of a TOF-SIMS apparatus including three ion sources (ions) is illustrated in FIG. 1. A TOF-SIMS apparatus 100 includes an ion source (ion) 101, an ion source (ion) 102, and an ion source (ion) 103. Each ion source (ion) can be used as an ion source (ion) for etching in the depth direction and/or a primary ion source (primary ion).

Note that analyses with the same TOF-SIMS apparatus using different ion sources (ions) are preferable. Thus, an influence of apparatus-dependent variations can be reduced. Note that one aspect of one embodiment of the present invention is not limited to this, and different TOF-SIMS apparatuses can be used. For example, a TOF-SIMS apparatus using the first primary ion source (primary ion) can be different from a TOF-SIMS apparatus using the second primary ion source (primary ion). Thus, the cost for introducing apparatuses can be reduced.

This embodiment is obtained by performing change, addition, modification, removal, application, superordinate conceptualization, or subordinate conceptualization on part or the whole of another embodiment. Thus, part of or the whole of this embodiment can be freely combined with, applied to, or replaced with part of or the whole of another embodiment.

Embodiment 5

In this embodiment, an example of handling a sample is described.

A sample in which a film for measurement is provided over a substrate is described as an example. In the depth profiling from above the substrate, in the case where an unnecessary film exists over the film for measurement, it is preferable that the unnecessary film be removed and then irradiation with ions (ion sources) for etching in the depth direction or primary ions (primary ion sources) be performed. That is, the depth profiling is performed from above downward. Note that part of the film for measurement may also be removed by removing the unnecessary film. In this case, the film for measurement which is attached to the unnecessary film can also be analyzed in the depth direction by TOF-SIMS, whereby the whole film for measurement can be analyzed.

Note that one embodiment of the present invention is not limited to this. For example, instead of analyzing from above a substrate, the bottom (the rear) of a substrate is polished, etched, or reduced to remove part or all of the substrate. Then, an analysis is performed from the surface by irradiating with ions for etching in the depth direction and primary ion sources. That is, depth profiling is performed from bottom upward. This eliminates the need for removing an unnecessary film over a film for measurement and thus an analysis can be performed more accurately.

This embodiment is obtained by performing change, addition, modification, removal, application, superordinate conceptualization, or subordinate conceptualization on part or the whole of another embodiment. Thus, part of or the whole of this embodiment can be freely combined with, applied to, or replaced with part of or the whole of another embodiment.

Note that in this specification and the like, when it is explicitly described that "Y is formed on X" or "Y is formed over X", it does not necessarily mean that Y is formed in direct contact with X. The description includes the case where X and Y are not in direct contact with each other, that is, the case where another object is placed between X and Y. Here, each of X and Y denotes an object (e.g., a device, an element, a circuit, a wiring, an electrode, a terminal, a conductive film, a layer, or the like).

Therefore, for example, when it is explicitly described that "a layer Y is formed on (or over) a layer X", it includes both the case where the layer Y is formed on and in direct contact with the layer X, and the case where another layer (e.g., a layer Z) is formed on and in direct contact with the layer X and the layer Y is formed on and in direct contact with the layer Z. Note that another layer (e.g., a layer Z) may be a single layer or a plurality of layers (a stack of layers).

Similarly, when it is explicitly described that Y is formed above X, it does not necessarily mean that Y is formed on and in direct contact with X, and another object may be placed between X and Y. Therefore, for example, when it is described that "a layer Y is formed above a layer X", it includes both the case where the layer Y is formed on and in direct contact with the layer X, and the case where another layer (e.g., a layer Z) is formed on and in direct contact with the layer X and the layer Y is formed on and in direct contact with the layer Z. Note that another layer (e.g., a layer Z) may be a single layer or a plurality of layers (a stack of layers).

Note that when it is explicitly described that Y is formed over, on, or above X, it includes the case where Y is formed obliquely over/above X.

Note that the same can be said when it is explicitly described that Y is formed below or under X.

For example, in this specification and the like, explicit singular forms preferably mean singular forms. However, without being limited thereto, such singular forms can include plural forms. Similarly, explicit plural forms preferably mean plural forms. However, without being limited thereto, such plural forms can include singular forms.

For example, in this specification and the like, the terms "first", "second," "third," and the like are used for distinguishing various elements, members, regions, layers, and areas from each other. Therefore, the terms such as "first", "second", "third", and the like do not limit the number of the elements, members, regions, layers, areas, or the like. Further, for example, "first" can be replaced with "second", "third", or the like.

For example, in this specification and the like, terms for describing spatial arrangement, such as "over", "above", "under", "below", "laterally", "right", "left", "obliquely", "behind", "front", "inside", "outside", and "in" are often used for briefly showing a relation between an element and another element or between a feature and another feature with reference to a diagram. Note that embodiments of the present invention are not limited thereto, and such terms for describing spatial arrangement can indicate not only the direction illustrated in a diagram but also another direction. For example, when it is explicitly described that "Y is over X", it does not necessarily mean that Y is placed over X. Since a device in a diagram can be inverted or rotated by 180°, the case where Y is placed under B can be included. Accordingly, "over" can refer to the direction described by "under" in addition to the direction described by "over". Note that the embodiments of the present invention are not limited to this, and "over" can refer to any of the other directions described by "laterally", "right", "left", "obliquely", "behind", "front", "inside", "outside", and "in" in addition to the directions described by "over" and "under" because the device in the diagram can be rotated in a variety of directions. That is, such terms can be construed as appropriate depending on circumstances.

Note that in this specification and the like, in a diagram or a text described in one embodiment, it is possible to take out part of the diagram or the text and constitute one embodiment of the invention. Thus, in the case where a diagram or a text related to a certain portion is described, the context taken out from part of the diagram or the text is also disclosed as one embodiment of the invention, and one embodiment of the invention can be constituted. Thus, for example, in a diagram or a text including one or more of active elements (e.g., transistors or diodes), wirings, passive elements (e.g., capacitors or resistors), conductive layers, insulating layers, semiconductor layers, organic materials, inorganic materials, components, devices, operating methods, manufacturing methods, or the like, it is possible to take out part of the diagram or the text and constitute one embodiment of the invention. For example, from a circuit diagram in which N circuit elements (e.g., transistors or capacitors; N is an integer) are provided, it is possible to constitute one embodiment of the invention by taking out M circuit elements (e.g., transistors or capacitors; M is an integer, where M<N). As another example, it is possible to constitute one embodiment of the invention by taking out M layers (M is an integer, where M<N) from a cross-sectional view in which N layers (N is an integer) are provided. As another example, it is possible to constitute one embodiment of the invention by taking out M elements (M is an integer, where M<N) from a flow chart in which N elements (N is an integer) are provided.

Note that in the case where at least one specific example is described in a diagram or a text described in one embodiment in this specification and the like, it will be readily appreciated by those skilled in the art that a broader concept of the specific example can be derived. Therefore, in the diagram or the text described in one embodiment, in the case where at least one specific example is described, a broader concept of the specific example is disclosed as one embodiment of the invention, and one embodiment of the invention can be constituted.

Note that in this specification and the like, a content described in at least a diagram (which may be part of the diagram) is disclosed as one embodiment of the invention, and one embodiment of the invention can be constituted. Therefore, when a certain content is described in a diagram, the content is disclosed as one embodiment of the invention even when the content is not described with a text, and one embodiment of the invention can be constituted. In a similar manner, part of a diagram, which is taken out from the diagram, is disclosed as one embodiment of the invention, and one embodiment of the invention can be constituted.

Example 1

In this example, results of a TOF-SIMS analysis using an analysis method which is one embodiment of the present invention are described.

Figure 2B:
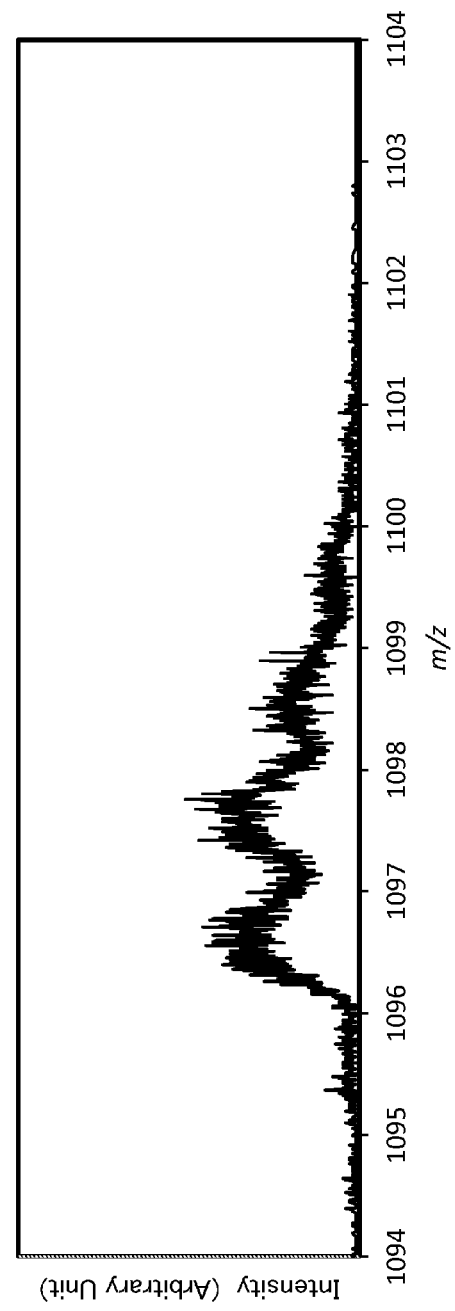

An organic EL element containing unknown components was used as a sample. TOF.SIMS 5 (manufactured by ION-TOF GmbH) was used. An analysis was performed using a gas cluster ion beam (GCIB) as a primary ion source and argon cluster ions. Note that irradiation with the primary ions was performed in a pulsed manner with a pulse width of 10645.9 ns. The current density (the irradiation amount) was $3.3 \times 10^{10}$ ions/cm$^2$, the acceleration voltage was 10 keV, and the current value was 0.02 pA. FIGS. 2A and 2B show the measurement results.

In addition, FIGS. 3A and 3B show results of measurement in which the same sample was measured in a manner similar to the above analysis and a bismuth cluster ion ($Bi_3^+$) was used as a primary ion source. Note that the measurement conditions were as follows: the pulse width was 15.2 ns, the current density (the irradiation amount) was $3.3 \times 10^{11}$ ions/cm$^2$, the acceleration voltage was 25 keV, and the current value was 0.2 pA.

As shown in FIG. 3A, in the analysis using $Bi_3^+$ as a primary ion, many signals are observed at and under m/z=200 and big signals are observed at m/z=901.45 and m/z=1096.54.

When the unknown sample was analyzed, it cannot be determined whether the signals at m/z=901.45 and m/z=1096.54 are derived from the same components in a precursor-product ion relationship or different components from each other.

Here, referring to FIG. 2A which shows a result of an analysis using argon cluster ions as a primary ion on the same sample, although a big signal is observed at m/z=1097.76, few signals are observed around m/z=900.

From this result, it can be found that the signal at m/z=901.45 in the analysis using $Bi_3^+$ as a primary ion is derived from a product ion fragmented by $Bi_3^+$.

Next, FIG. 2B is referred to. FIG. 2B is a chart in which the range of from m/z=1094 to m/z=1104 in FIG. 2A is enlarged. From this chart, it is found that although the object for measurement is less broken, the resolution is low in the measurement using argon cluster ions. Here, referring to FIG. 3B in which the range of from m/z=1094 to m/z=1104 in FIG. 3A which is the result of an analysis using $Bi_3^+$ is enlarged, it can be found that isotope peaks are clearly separated and a main peak is at m/z=1096.52.

As described above, by referring to both the result of an analysis using an argon cluster ion as a primary ion which does not easily break molecules contained in a sample and the result of an analysis using $Bi_3^+$ as a primary ion with high resolution, even in an unknown sample, molecular weight of the contained material can be accurately predicted.

This application is based on Japanese Patent Application serial No. 2012-099032 filed with Japan Patent Office on Apr. 24, 2012, the entire contents of which are hereby incorporated by reference.

What is claimed is:

1. An analysis apparatus comprising:
   a first ion source, the first ion source being configured to irradiate a sample with a first primary ion;
   a second ion source, the second ion source being configured to etch the sample in a depth direction and to irradiate the sample with a second primary ion; and
   a detector, the detector being configured to obtain first mass spectral data and to obtain second mass spectral data at the same time.

2. The analysis apparatus according to claim 1,
   wherein the second primary ion comprises a cluster ion including a plurality of atoms, and
   wherein a second number of atoms of the second primary ion is larger than a first number of atoms of the first primary ion.

3. The analysis apparatus according to claim 1,
   wherein a first number of fragment peaks of the first mass spectral data is larger than a second number of fragment peaks of the second mass spectral data.

4. The analysis apparatus according to claim 1,
   wherein a first secondary ion is released from the sample,
   wherein a second secondary ion is released from the sample,
   wherein the first spectral data is obtained from a flight time of the first secondary ion, and
   wherein the second spectral data is obtained from a flight time of the second secondary ion.

5. An analysis method using TOF-SIMS, comprising the steps of:
   obtaining first mass spectral data by irradiating a sample with a first primary ion;
   obtaining second mass spectral data by irradiating the sample with a second primary ion; and
   evaluating components of the sample by comparing the first mass spectral data with the second mass spectral data,
   wherein a first number of fragment peaks of the first mass spectral data is larger than a second number of fragment peaks of the second mass spectral data, and
   wherein the obtaining the first mass spectral data and the obtaining the second mass spectral data are performed at the same time.

6. The analysis method using TOF-SIMS according to claim 4,
   wherein the second primary ion comprises a cluster ion including a plurality of atoms, and
   wherein a second number of atoms of the second primary ion is larger than a first number of atoms of the first primary ion.

7. The analysis method using TOF-SIMS according to claim 5,
   wherein a first secondary ion is released from the sample,
   wherein a second secondary ion is released from the sample,
   wherein the first spectral data is obtained from a flight time of the first secondary ion, and
   wherein the second spectral data is obtained from a flight time of the second secondary ion.

8. An analysis method using TOF-SIMS, comprising the steps of:
   obtaining first mass spectral data by irradiating a sample with a first primary ion;
   obtaining second mass spectral data by irradiating the sample with a second primary ion;
   etching a surface of the sample by an ion and then irradiating the surface of the sample with the first primary ion or the second primary ion; and
   evaluating components of the sample by comparing the first mass spectral data with the second mass spectral data,
   wherein a first number of fragment peaks of the first mass spectral data is larger than a second number of fragment peaks of the second mass spectral data.

9. The analysis method using TOF-SIMS according to claim 8,
   wherein the second primary ion comprises a cluster ion including a plurality of atoms, and
   wherein a second number of atoms of the second primary ion is larger than a first number of atoms of the first primary ion.

10. The analysis method using TOF-SIMS according to claim 8,
    wherein the obtaining the first mass spectral data and the obtaining the second mass spectral data are performed at the same time.

11. An analysis method using TOF-SIMS, comprising the steps of:
    obtaining first spectral data by irradiating a sample with a first primary ion;
    obtaining second spectral data by irradiating the sample with a second primary ion;
    etching a surface of the sample by an ion including the same element as the second primary ion; and
    evaluating components of the sample by comparing the first mass spectral data with the second mass spectral data,
    wherein a first number of fragment peaks of the first mass spectral data is larger than a second number of fragment peaks of the second mass spectral data.

12. The analysis method using TOF-SIMS according to claim 11,
    wherein the second primary ion comprises a cluster ion including a plurality of atoms, and
    wherein a second number of atoms of the second primary ion is larger than a first number of atoms of the first primary ion.

13. The analysis method using TOF-SIMS according to claim 11,
    wherein the obtaining the first mass spectral data and the obtaining the second mass spectral data are performed at the same time.

14. The analysis method using TOF-SIMS according to claim 8,
    wherein a first secondary ion is released from the sample,
    wherein a second secondary ion is released from the sample,
    wherein the first spectral data is obtained from a flight time of the first secondary ion, and
    wherein the second spectral data is obtained from a flight time of the second secondary ion.

15. The analysis method using TOF-SIMS according to claim 11,
   wherein a first secondary ion is released from the sample,
   wherein a second secondary ion is released from the sample,
   wherein the first spectral data is obtained from a flight time of the first secondary ion, and
   wherein the second spectral data is obtained from a flight time of the second secondary ion.

* * * * *

UNITED STATES PATENT AND TRADEMARK OFFICE
CERTIFICATE OF CORRECTION

| | | |
|---|---|---|
| PATENT NO. | : 8,772,712 B2 | Page 1 of 1 |
| APPLICATION NO. | : 13/863698 | |
| DATED | : July 8, 2014 | |
| INVENTOR(S) | : Hajime Kimura et al. | |

It is certified that error appears in the above-identified patent and that said Letters Patent is hereby corrected as shown below:

In the Claims,

In claim 6, at column 19, line 55, "4," should be --5,--.

Signed and Sealed this
Ninth Day of December, 2014

Michelle K. Lee
*Deputy Director of the United States Patent and Trademark Office*